United States Patent [19]

Santini

[11] Patent Number: 5,118,810

[45] Date of Patent: Jun. 2, 1992

[54] PROCESS FOR PREPARING ALDEHYDES FROM BASE SENSITIVE AMINES

[75] Inventor: Conrad Santini, Warren, N.J.

[73] Assignee: Merck & Co., Inc., Rahway, N.J.

[21] Appl. No.: 549,040

[22] Filed: Jul. 6, 1990

[51] Int. Cl.$^5$ .............................................. C07D 417/06
[52] U.S. Cl. ..................................... 548/181; 548/479
[58] Field of Search ....................... 548/201, 181, 479

[56] References Cited

U.S. PATENT DOCUMENTS 4,661,479  4/1987  Wyuratt ............................ 514/214

OTHER PUBLICATIONS

Potts, Comprehensive Heterocyclic Chemistry, vol. 6, p. 320 (1984).

Buckley JACS 104, 4446 (1982).
March, Advanced Organic Chemistry, pp. 312,387,1081,1082 (1985).

Primary Examiner—Robert Gerstl
Attorney, Agent, or Firm—William H. Nicholson; Joseph F. DiPrima

[57] ABSTRACT

There is disclosed a process for preparing aldehydes from base sensitive amines. The process can be employed to obtain carboxylic acid methyl esters. In particular, thiazolidine carboxylic methyl ester can be produced which is useful as an intermediate in the preparation of bicyclic lactam compounds. These bicyclic lactam compounds are potent angiotesin converting enzyme (ACE) inhibitors useful in the treatment of hypertension, congestive heart failure, and the like.

2 Claims, No Drawings

PROCESS FOR PREPARING ALDEHYDES FROM BASE SENSITIVE AMINES

BACKGROUND OF THE INVENTION

This invention is directed to a process for preparing aldehydes from base sensitive amines. The process can be employed to obtain carboxylic acid methyl esters; in particular, thiazolidine carboxylic acid methyl ester which is useful as an intermediate in the preparation of bicyclic lactams. These bicyclic lactam compounds are potent angiotensin converting enzyme (ACE) inhibitors useful in the treatment of hypertension, congestive heart failure, and the like. (See, for example, U.S. Pat. Nos. 4,415,496; 4,661,479; and 4,371,444).

One prior art process discloses the preparation of an aldehyde which is then coupled with cysteine methyl ester to obtain a thiazolidine methyl ester [J. Biol. Chem, 198, 765 (1952); ibid, 192, 535 (1951)]. This process requires a long, cumbersome sequence involving enzymatic resolution of racemic material to obtain the desired thiazolidine intermediate. The final product is produced in low yields (~3%) which is not commerically or economically attractive.

In another prior art process, an aldehyde surrogate is produced which is then coupled with cysteine methyl ester from which the desired thiazolidine product is obtained in low yields (~10%–20%) only after prolonged and intensive chromatographic purification [JACS, 46, 1937 (1981)].

SUMMARY OF THE INVENTION

It has now been found that the low yielding, prolonged and commerically uneconomical prior art methods used to obtain the desired aldehyde products are overcome by using the process of this invention. The process of this invention is more economical than prior art processes; involves fewer process steps; shorter reaction time; and results in obtaining the desired aldehyde product in significantly higher, commercially attractive yields without purification of intermediates or final product.

In general, the process of the invention comprises:

(a) converting a terminally protected amine to a fully protected amine ester;

(b) selectively deblocking said fully protected amine ester and treating it with a metal halide in a suitable solvent to obtain a halide compound;

(c) oxidizing said halide compound to obtain an aldehyde ester;

(d) reducing said lysine aldehyde ester to obtain an aldehyde acid; and, if desired, coupling said aldehyde acid with a methyl ester to obtain a carboxylic acid methyl ester compound.

Thus, the process of the invention involves the conversion of base sensitive amines to aldehydes; that is, amines whose functionality (optical activity) are disturbed by exposure to bases. Illustrative base sensitive amines that can be used in the process of the invention are such compounds as optically active amino carbonyl compounds, amino esters of methanol or amino alcohols containing acetyl groups, amino carbonyl compounds having more than one stereo center (i.e., racemaic or optically active), amines containing groups other than a halide which are easily removable; amines containing strained rings (e.g., 4-membered rings) that are subject to ring opening, and the like.

The protecting groups that can be used in the process of the invention are those that can be readily removed by acid or reduction. Illustrative of such protecting groups are carbamates such as benzyl carbamate (t-butyl carbamate, methyl carbamate, 2,2,2-trichloroethyl carbamate, 2-iodoethyl carbamate, vinyl carbamate, and the like), benzamide, phthalamide, 2,3-diphenylmalamide, N-phenacylmethyl, benzyl, and the like. Preferably, the protecting groups used are those that are commerically available such as carbobenzyloxy (CBz), butoxycarbonyl (BOC), phthaloyl (Pht), and the like.

The process of the invention is further illustrated in the following reaction scheme in which a thiazolidine carboxylic acid methyl ester compound is obtained.

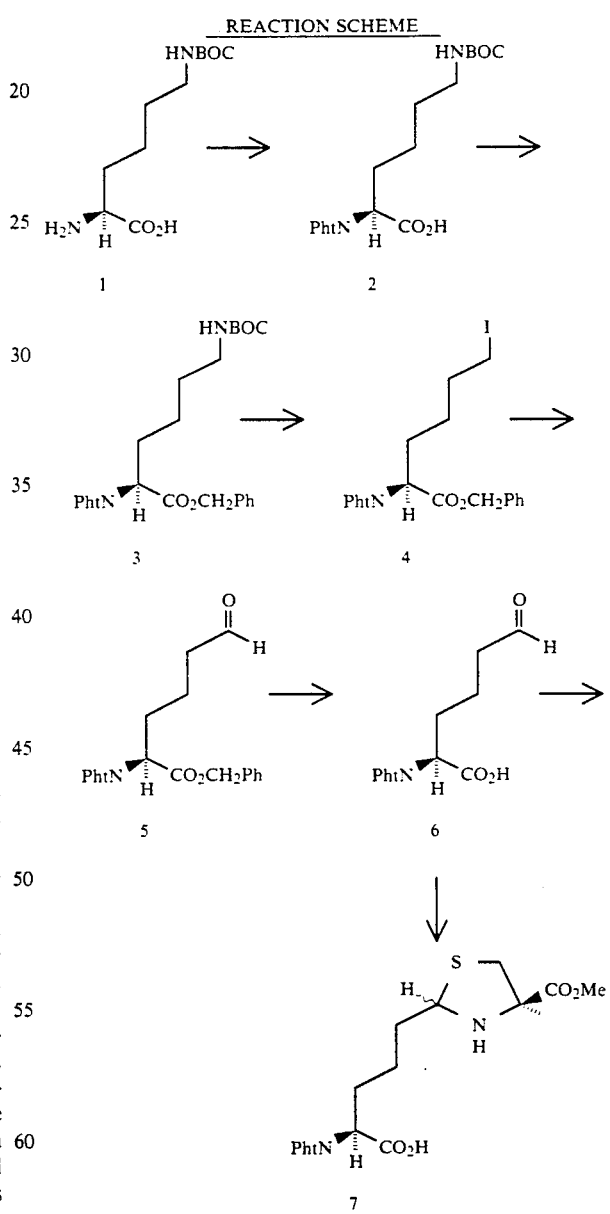

Ph = phenyl

As shown in the reaction scheme, terminally protected lysine; i.e., ε-BOC-L-lysine, 1 is converted to its doubly protected acid derivative 2 under basic conditions using sodium carbonate and N-carbethoxyphthalimide in water/ethanol (2:1) at ambient temperature. Acid 2 is then esterified to the novel, fully protected lysine ester 3 using cesium carbonate and benzyl bromide in dimethylformamide (DMF) at ambient temperature. Novel ester 3 is then selectively deblocked using dry hydrogen chloride in isopropyl acetate at an elevated temperature of about 45° C. followed by activating the deblocked product by treating it with trifluoromethanesulfonic anhydride (2 equivalents) and diisopropylethylamine (3 equivalents) in methylene chloride at a temperature of from about −78° C. to about 25° C. The methylene chloride is then evaporated and the resulting residue dissolved in sodium iodide (1M) in acetonitrile (10 equivalents) and stirred at ambient temperature to obtain isolated primary iodide 4. Primary iodide 4 is then dissolved in dimethylsulfoxide (DMSO) with diisopropylethylamine (2 equivalents) and heated at an elevated temperature of from about 60° C. to about 100° C., under an inert atmosphere and in a partial vacuum (∼250 mmHg) to effect concurrent removal of the dimethylsulfoxide by-product and obtain aldehyde ester 5. Ester 5 is then desulferized by treating it with Raney nickel followed by hydrogenation with 10% Pd/C in ethanol at about 3 atmospheres (40 psi) to remove the benzyl group and afford aldehyde acid 6. Aldehyde acid 6 is then coupled with L-cysteine methyl ester in tetrahydrofuran (THF) to afford the 2-substituted thiazolidine-4-carboxylic acid methyl ester 7.

Although the conversion of protected lysine 1 to acid 2 occurs under basic conditions, any base can be used. Similarly, while any appropriate gas can be employed during the deblocking of novel ester 3, hydrogen chloride is preferred as it is easily removable and does not interfere with the subsequent reaction. However, the use of a reagent in sufficient quantity and powerful enough to activate the amino group in the activation of novel ester 3 is necessary. For this activation step, the use of 2 molar equivalents of a reagent such as trifluoromethanesulfonic anhydride is most preferred. Also, during activation of novel ester 3, a neutral solvent, such as a chlorinated solvent, is preferred to avoid unnecessary reactions with the other reagents.

The use of sodium iodide and acetonitrile in obtaining primary iodide 4 are not critical as any metal halide and a non-nucleophilic solvent (e.g., DMF) could readily be used. Similarly, the use of DMSO as solvent and diisopropylethylamine are not critical as any suitable solvent and tertiary amine can be employed. After primary iodide 4 is isolated, however, it is preferred that its subsequent treatment to obtain aldehyde ester 5 be accomplished without delay (preferably within 2 hours) to prevent deterioration of iodide 4 which, in turn, would result in reduced yields of the desired thiazolidine product 7.

When a non-sulfur containing solvent is used to dissolve primary iodide 4, then the use of a desulferizing agent such as Raney nickel would not be required as sulfur-containing by-products would not form thereby necessitating their removed. However, the use of the sulfur-containing DMSO solvent is preferred as it was found to result in higher yields of aldehyde acid 6 which, in turn, provides greater yields of thiazolidine methyl ester 7.

In the debenzylation of aldehyde ester 6 and its conversion to thiazolidine methyl ester 7, the use of palladium on carbon (Pd/C) as catalyst and ethanol as solvent are not critical as any sutiable catalyst and solvent can be used during this coupling reaction.

Thus, the process of the invention can be used to convert optically pure ε-BOC-L-lysine to a pair of pure thiazolidine diasteriomers which, in turn, are useful intermediates in the preparation of bicyclic lactam ACE inhibitor compounds.

DETAILED DESCRIPTION OF THE INVENTION

The following examples are set forth to further illustrate the process of the invention and, as such, they are not intended nor should they be construed as limiting the invention set forth in the appended claims.

EXAMPLE 1

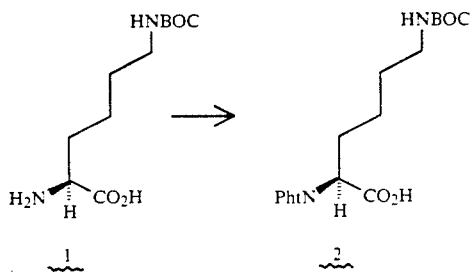

A 22 l. 3-neck flask was equipped with a mechanical stirrer and charged with 10 liters of water and 946.14 g of ε-BOC-L-lysine (1). The suspension was stirred and treated with 5 liters of ehtanol and 363.14 g of solid anhydrous sodium carbonate. The suspension, which spontaneously warmed to 35° C., was stirred for 4 hours by which time dissolution was nearly complete. The turbid solution was treated with 751.4 g of solid 2-carbethoxy phtalimide and stirred overnight at 25° C.

At the end of this time, the turbid solution was drawn from the flask and stripped free of ethanol. The remaining aqueous layer (pH=9) was washed twice with 2 liter portions of ethyl acetate. After separation, the aqueous layer was vigorously stirred with 5 liters of methylene chloride and treated with 6N HCl until the pH was 2.75. Stirring was stopped and the thick, gelatinous lower layer was drawn off. Another 5 liters of methylene chloride were added along with 3 liters of brine and the mixture was vigorously stirred. The highly emulsified mixture was allowed to separate and the lower layer drawn off.

The combined organics were stripped free of methylene chloride and redissolved in 12 liters of ethyl acetate. The still gelatinous organic layer was washed with 1 liter of brine, the layers quickly separating.

The aqueous layers were washed with 2 liter portions of ethyl acetate until no product was detectable by high pressure liquid chromatography (HPLC). The combined organics were dried over sodium sulfate and filtered through a fine particulate filter. Removal of ethyl acetate afforded a viscous semi-solid (wt=1,472.6 g).

A sample of the residue was removed and weighed. After pumping under high vacuum for 1 hour, it was determined that 86.9% of the crude product was non-volatile. Nuclear magnetic resonance (NMR) analysis indicated the non-volatile material was 83.6% product by weight. Therefore, the crude product was 72.6% desired acid (2) by weight (1069.1 g; 82.9% yield). The product 2 was used without further purification.

EXAMPLE 2

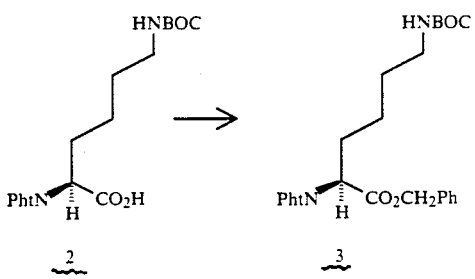

1,472.6 Grams of crude N-α-phtalimido-N-ε-BOC-L-lysine, known to contain 1069.1 g of desired acid 2 were dissolved in 4 liters of sieve-dry DMF and allowed to turn under vacuum in a rotary evaporator for 45 minutes to remove most of the residual ethyl acetate. The solution was transferred to a 12 liter 3-neck flask having a mechanical stirrer. Another 4 Liters of dry DMF were added, followed by 926.25 g of solid cesium carbonate. After stirring at 25° C. for 15 minutes, 482.6 g of benzyl bromide were added and the mixture was stirred overnight.

At the end of this time thin layer chromatography (TLC) (ethyl acetate) showed no benzyl bromide remained. 4 Liters of the reaction mixture were drawn from the flask and partitioned between 1.5 liters of saturated sodium bicarbonate and 8 liters of tert-butyl methyl ether. The layers were separated and the organic washed twice more with 1.5 liter portions of aqueous bicarbonate, followed by four washes with 1.5 liter portions of water. This procedure was repeated for the rest of the reaction mixture.

The combined aqueous layers were extracted once with 4 liters of tert-butyl methyl ether. The combined organics were dried over magnesium sulfate, filtered and stripped to an oil (wt=1,243.4 g). NMR revealed a residual amount of solvent equal to 10.3% weight. The remaining non-volatile material was found to be 96.5% desired product 2 by weight, thus indicating the oil to be 86.6% desired ester 3 by weight (1076.8 g; 81.3% yield). The material was used without further purification.

EXAMPLE 3

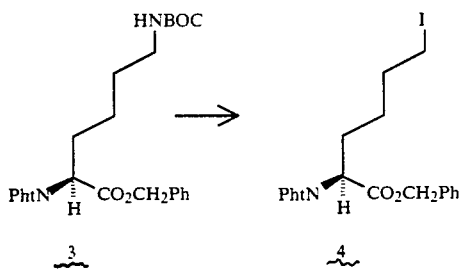

1,234.4 Grams of crude α-phtalimide-ε-BOC-L-lysine benzyl ester, known to contain 1,076 g desired material 3 were dissolved in 13 liters of isopropyl acetate and placed in a 22 liter 3-neck flask equipped with a mechanical stirrer, a gas inlet tube which extended below the surface of the solution, and an outlet adapter. The outlet was connected via tubing to the straight neck of an adapter which, in turn, was affixed atop a reflux condenser (3 feet long). The curved side arm of the adapter was left open and into it was placed a tube delivering a strong stream of cold tap water. The condenser was mounted such that it sat vertically above a floor drain. The effluenet gas from the reaction was thus mixed with water in the condenser and allowed to pass into the drain. The pH of the water was monitored at the bottom of the condenser with pH paper.

The inlet tube was connected to a 2 lb. cylinder of hydrogen chloride. With rapid stirring, hydrogen chloride was passed in until the isopropyl acetate was essentially saturated at which point solvent was observed in the outlet tube and the pH of the water was strongly acidic to litmus. The homogeneous solution was stirred for 1 hour (wt of added HCl=705 g).

At the end of this time, the water trap was removed and replaced with a 5000 ml round bottom flask having a trap adapter and containing 3000 ml of water. A 1000 ml round bottom flask with trap adapter was placed between the reaction vessel and water trap to prevent suck-back. The entire apparatus was evacuated to partial vacuum (20 mm) to remove excess gaseous HCl.

When bubbling of HCl was no longer evident, the solution (now pink) was stripped free of isopropyl acetate under vacuum on a large rotary evaporator to give a viscous white oil. 2 Liters of anhydrous ether were added and stirred at top speed on the rotary concentrator without vacuum for 3 minutes. The ether was decanted and 2 liters of methylene chloride were added, then stripped off in the same way to leave a white foam which was stored at 10° C. overnight. The foam was then dissolved in 8.5 liters of sieve-dry methylene chloride and placed in a 22 liter 3-neck flask equipped with a mechanical stirrer, nitrogen inlet atop a 2000 ml dropping funnel, and a thermocouple temperature probe. The solution was cooled to −76° C. and the dropping funnel was charged with 896 g of diisopropylethylamine. The amine (1207.5 ml) was then added dropwise to the methylene chloride mixture over a period of 30 minutes.

While the amine addition was proceeding, a dry 1000 ml dropping funnel was charged with 777 ml of trifluoromethane sulfonic anhydride by canula. When the amine was all added, the dropping funnels were switched and the sulfonic anhydride added at a rate such that the internal temperature did not exceed −60° C. After addition was complete, the cold bath was bailed out and the reaction mixture warmed to 25° C.

The dropping funnel, thermocouple and gas inlet were removed and replaced with 2 outlet adapters connected through vacuum tubing to a large cold trap connected to vacuum. With warming to room temperature, the methylene chloride was pumped off leaving a brown oil. The oil was dissolved in 12 liters of acetonitrile and treated with 3.32 kg of solid sodium iodide. The resulting turbid solution was stirred for 3 hours at 25° C.

At the end of this time, the solution was drawn from the flask and stripped free of acetonitrile. The resulting mixture was partitioned between water and 50% hexane in methylene chloride. The oily amine salts were separated and set aside for separate workup. After the layers were separated, the water was extracted with hexane/methylene chloride (1:1). The oily salts were extracted 3 times with equal volumes of hexane/methylene chloride, then again set aside. The combined organics were washed with pH 2 water three times, then dried, filtered and stripped to a yellow-brown residue (wt. 988.7 g). The oily salts were dissolved in 500 ml of isopropyl acetate and extracted with 1 liter of hexane four times. The supernatant was dried, filtered and stripped to a pale yellow residue (wt. 42.8 g).

HPLC assay of the main isolate indicated 65% desired iodide 4 by weight. NMR analysis indicated a 11.6:1.6:1 mixture of desired iodide:alcohol (from hydrolysis):trifluoromethane sulfonamide. Total yields were 61% iodide, 8.5% alcohol and 5.3% amide. The material was used without further purification.

EXAMPLE 4

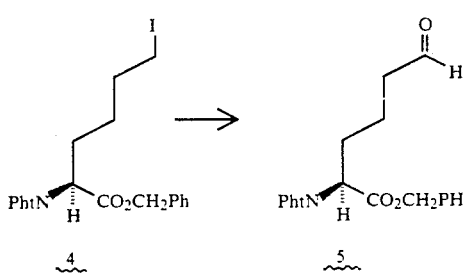

A 22 liter 3-neck flask was placed in a heating mantle and equipped with a mechanical stirrer. One sidearm was fitted with an adapter, the straight neck of the adapter having a rubber septum through which a thermocouple temperature sensing probe was passed in the solution. The curved neck was fitted with a teflon stopcock gas inlet adapter connected to a regulated nitrogen source. The other sidearm was fitted with a distillation head having a water cooled condenser and 500 ml receiver flask. The outlet from the distillation head was connected with vacuum tubing to an empty 1000 ml round bottom flask equipped with a trap adapter and then a 5000 ml flask/trap adapter containing 1 gallon of liquid chlorine bleach which was magnetically stirred. The bleach trap was connected along with a vacuum gauge to a vacuum source.

998.7 Grams of crude 2-L-phtalimido-6-iodo hexanoic acid benzyl ester, known to contain 649.2 g of product 4, were dissolved in 13 liters of sieve-dry DMSO and placed in the flask. A partial vacuum/purge environment was created by applying vacuum, then bleeding in 5 p.s.i. of nitrogen, causing a rapid sweep of gas through the entire apparatus. This was done following addition of 475 ml of diisopropylethylamine.

The solution was heated to 80° C. and stirred for 2.5 hours. During this time, the amine was observed distilling out a 50° C. To prevent depletion of the base, fresh diisopropylethylamine (DIEA) was added every 5 minutes by syringe at the rate of 1 equivalent/hr.

At the end of this time, the reaction was cooled to 25° C. The reaction mixture was drawn from the flask in 3 portions and stirred with 8 liters of water and 6 liters of tert-butyl methyl ether. Each time the aqueous layer was drawn off, the organic layer was left in the extraction apparatus. The organic layer was set aside after the last portion of reaction mixture was extracted. The combined aqueous layers were divided into 3 portions and each portion was extracted with 2×2 liter portions of ether. The organics were combined and washed with the following: 2×2 liter H2O; 4×1 liter pH 2.5 water; 1×2.0 liter saturated aqueous sodium bicarbonate. The organics were dried, filtered and stripped to a residue (wt.=638.4 g). HPLC analysis indicated the crude residue was 49% desired aldehyde 5 by weight (312.8 g; 63% yield). NMR showed the existance of the alcohol in a 1:3.33 ratio to aldehyde (93.9 g). The material was used without further purification.

EXAMPLE 5

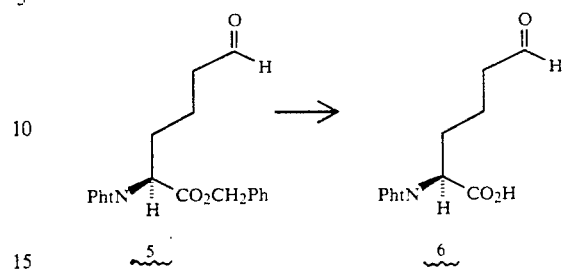

607.6 Grams of crude 2-L-phtalimido adipic acid monoaldehyde benzyl ester, known to contain 312.8 g of desired ester 5, were dissolved in 10 liters of absolute ethanol and placed in a 22 l motor-stirred extraction apparatus. The brown solution was treated with 1.5 kg of activated Raney nickel in ethanol (DANGER! SPONTANEOUS IGNITION). The mixture was vigorously stirred for 2 hours.

The resultant slurry was drained from the apparatus and filtered through a fine particulate filter. The filtrate was concentrated to a yellow oil (wt=456.1 g).

The residue was dissolved in 8 liters of absolute ethanol and divided into 2 equal portions. Each portion was hydrogenated over 45.6 g 10% Pd/C at 40 p.s.i. for 6.5 hours. At the end of this time, the solutions were combined and filtered free of catalyst through a fine particulate filter and stripped to a light green oil (wt=352.5 g). NMR showed a 3.3:1 mixture of desired aldehyde acid/alcohol acid 6. The material was used without further purification.

EXAMPLE 6

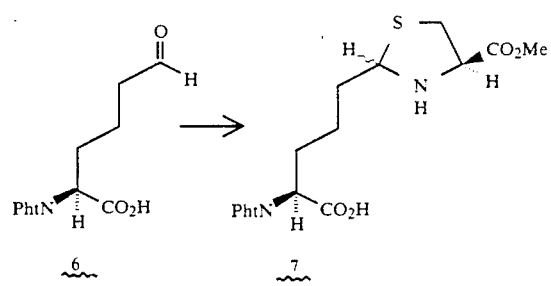

220.1 Grams of L-cysteine methyl ester hydrochloride were placed in a 12 liter 3-neck flask with a mechanical stirrer and 2 liter dropping funnel. The solid hydrochloride was suspended in 2 liters of tetrahydrofuran (THF). The dropping funnel was charged with 223 ml of DIEA. After cooling the suspension to 0° C., the amine was added over a 15 minute period.

The dropping funnel was then charged with 352.6 g of crude L-2-phtalimido adipic acid monoaldehyde dissolved in 2 liters of THF. The contents of the dropping funnel were added over a 20 minute period whereupon the cold bath was removed and the mixture stirred at 25° C. for 1.5 hours.

At the end of this time, the heterogeneous mixture was drawn from the flask and stripped free of solvent. The resultant oil was partitioned between 15 liters of 1:1 water/methylene chloride (pH aq.=5.90). After vigorous stirring, the layers were separated and the organic layer set aside. The remaining aqueous layer was vigorously stirred with 6 L. of methylene chloride and adjusted to pH 2.85 with 2N hydrochloric acid and the layers were then separated.

The organic layers isolated from each were rewashed at the pHs indicated above. The resultant aqueous layers from each wash were re-extracted to reduce cross-contamination of the desired thiazolidine and the alcohol from the previous step.

The pH 6 washes were combined and stripped to an oil (wt=329.7 g). NMR indicated a diastereomeric pair corresponding to 2-(4-L-phtalimido-5-pentanoic acid)-thiazolidine-L-4-carboxylic acid methyl ester 7 (50% by weight; 159.5 g; 64.7% yield from calculated amount of L-2-phtalimido adipic acid and monoaldehyde benzyl ester).

What is claimed is:

1. A process for preparing the compound of structure 6

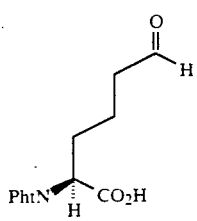

which comprises the steps of:

(a) treating a compound of structure 1

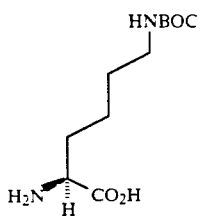

with sodium carbonate and N-carbethoxyphthalimide in a water/ethanol solvent at ambient temperature to provide the compound of structure 2;

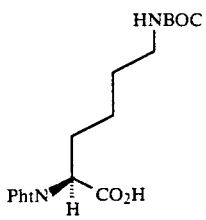

(b) treating the product of step (a) with cesium carbonate and benzyl bromide in DMF to provide the benzyl ester 3;

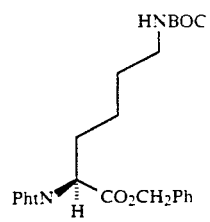

(c) treating the product of step (b) with dry hydrogen chloride in isopropyl acetate at an elevated temperature to selectively deblock the terminally protected base sensitive amine, treating the base sensitive amine with trifluoromethanesulfonic anhydride and diisopropylethylamine in methylene chloride at −78° C. to 25° C., evaporating the solvent and treating the residue with sodium iodide in acetonitrile at ambient temperature to provide the primary iodide 4;

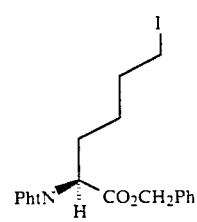

(d) treating the primary iodide in DMSO with diisopropylethylamine at 60° C. to 100° C. and partial vacuum to obtain the aldehyde ester 5

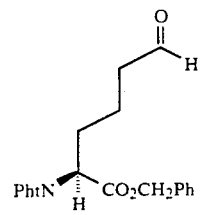

(e) treating the aldehyde ester with hydrogen over a 10% Pd/C catalyst to deesterify the ester and yield the aldehyde acid 6

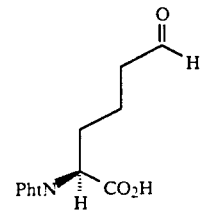

2. A process for preparing the compound of structure 7:

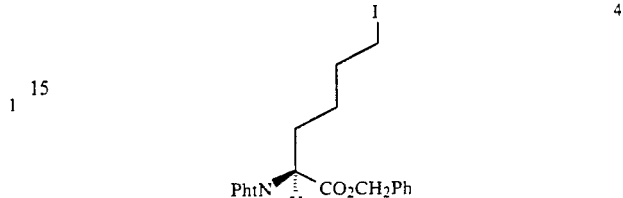

(c) treating the product of step (b) with dry hydrogen chloride in isopropyl acetate at an elevated temperature to selectively deblock the terminally protected base sensitive amine, treating the base sensitive amine with trifluoromethanesulfonic anhydride and diisopropylethylamine in methylene chloride at −78° C. to 25° C., evaporating the solvent and treating the residue with sodium iodide in acetonitrile at ambient temperature to provide the primary iodide 4;

which comprises the steps of:
(a) treating a compound of structure 1

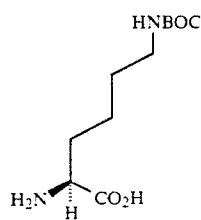

with sodium carbonate and N-carbethoxyphthalimide in a water/ethanol solvent at ambient temperature to provide the compound of structure 2;

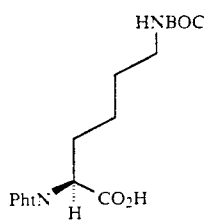

(b) treating the product of step (a) with cesium carbonate and benzyl bromide in DMF to provide the benzyl ester 3;

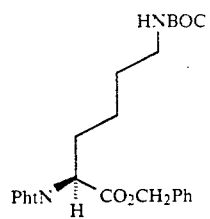

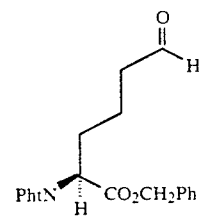

(d) treating the primary iodide in DMSO with diisopropylethylamine at 60° C. to 100° C. and partial vacuum to obtain the aldehyde ester 5

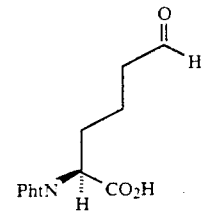

(e) treating the aldehyde ester with hydrogen over a 10% Pd/C catalyst to deesterify the ester and yield the aldehyde acid 6

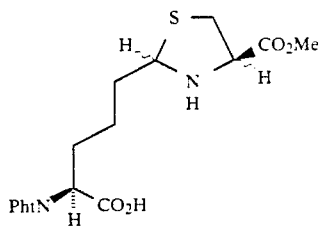

(f) and treating aldehyde 6 with L-cysterine methyl ester hydrochloride in THF and diisopropylethylamine at 0° C. to produce compound 7.

* * * * *